United States Patent [19]

Schmidt et al.

[11] Patent Number: 5,679,955

[45] Date of Patent: Oct. 21, 1997

[54] SPECTROSCOPIC METHOD

[75] Inventors: Stefan Schmidt, Genève; Luc Thévenaz, Yverdon-les-Bains, both of Switzerland

[73] Assignee: Orbisphere Laboratories Neuchatel, Neuchatel, Switzerland

[21] Appl. No.: 688,802

[22] Filed: Jul. 31, 1996

Related U.S. Application Data

[60] Provisional application No. 60/002806, Aug. 25, 1995.

[51] Int. Cl.⁶ .......................... G01N 21/17; G01N 21/61
[52] U.S. Cl. .................................. 250/343; 250/252.1
[58] Field of Search ........................ 250/252.1, 339.12, 250/343

[56] References Cited

U.S. PATENT DOCUMENTS

| | | | |
|---|---|---|---|
| 4,228,192 | 10/1980 | Sanden | 250/339.12 X |
| 4,445,359 | 5/1984 | Smith | 250/343 X |
| 5,387,971 | 2/1995 | Koashi et al. | 250/344 X |

FOREIGN PATENT DOCUMENTS 9317324  9/1993  WIPO .......................... 250/339.12

OTHER PUBLICATIONS

Fellows, Tim, "In–line alcohol and OC measurement . . . technology", Aug. 1993, pp. 24–29.
Gallignani, Maximo et al., "Stopped–flow near–infrared . . . beers", 1994, pp. 155–161.
Lau, Oi–Wah et al., "Spectrophotometric method for the determination . . . reagent" 1994, pp. 469–472.
McNab—Model KSB Alcohol Analyzer. (No Date).
Teass, H.A. (Bud), "Unique Full Diameter . . . Breweries", vol. 32, No. 3, 1995, pp. 169–174.

*Primary Examiner*—Edward J. Glick
*Attorney, Agent, or Firm*—Wigman, Cohen, Leitner & Myers, P.C.

[57] ABSTRACT

A method and apparatus serve to determine spectroscopically a concentration of ethanol in a test sample of an alcoholic aqueous beverage. The determination is based upon providing calibration data which establish a relation between (A) a plurality of transmission values of an electromagnetic radiation in the near infrared region, measured at a unique wavelength at which water is relatively opaque to the radiation while ethanol is relatively transparent thereto, of a plurality of calibration samples of the beverage containing ethanol in differing known concentrations, and (B) the known concentrations of ethanol in the calibration samples. Then, at least one light transmission value of the test sample at the unique wavelength, at which said calibration data were established, is measured. The measured transmission value of the test sample is transformed, by way of the relation established by the calibration data, into an indication of the concentration of ethanol in the test sample.

4 Claims, 2 Drawing Sheets

SPECTROSCOPIC METHOD

This application claims the benefit of U.S. Provisional application Ser. No. 60/002,806 filed Aug. 25, 1995.

FIELD OF THE INVENTION

The present invention generally relates to spectroscopy and, specifically to a spectroscopic method for determining a concentration of ethanol in a test sample of an alcoholic beverage that contains a major amount of water.

THE PRIOR ART

Spectroscopy, or spectral analysis, is a conventional method applied in qualitative and quantitative methods to determine components, or component concentration, of a sample.

Also, spectroscopy has been applied to determine the ethanol content of aqueous samples, notably in the brewing industry (cf. Fellows, T., In-line alcohol and OG measurement using near infrared technology, Brewers' Guardian, August 1993; incorporated herein by way of reference for all purposes), and suitable analyzers are available commercially (e.g. Model KSB Alcohol Analyzer provided by McNab Inc, Mount Vernon N.Y., U.S.A.).

A feature common to prior art methods of determining the concentration of ethanol in an aqueous sample is that they are based upon scanning absorption values of the sample over a range of wavelengths in the near infrared region and determining the ethanol concentration from an evaluation based upon significant peaks of the specific absorption of ethanol. This involves relatively complicated evaluation means, both with regard to the method as well as with regard to the apparatus.

OBJECTS AND SUMMARY OF THE INVENTION AND DEFINITIONS

Accordingly, it is a main object of the invention to provide for a method of determining the concentration of ethanol in an aqueous sample which is less complicated to operate and can be carried out with a more simple apparatus.

Surprisingly, it has been found that absorption measurement of light at a single wavelength is sufficient to achieve the above aim by what, according to the invention, can be termed "inverse" spectroscopy in the sense that absorption of the sample is measured at a wavelength where the substance of interest, or "analyte", i.e. ethanol, absorbs the radiation used to a significantly lesser degree than the aqueous phase or, in other words, is relatively transparent in relation to the aqueous phase, while the latter is relatively opaque and absorbs the radiation to a significantly larger degree.

In practice, it is possible according to the invention to work with transmitted light intensities directly, i.e., without actually calculating absorption.

As will be apparent to those experienced in the art of spectroscopy, such a simplified approach based upon "inverse" spectroscopy is anything but obvious because, conventionally, one would look for significant absorption of the substance of interest, i.e. the analyte, rather than the opposite. At the same time, it will be apparent that practical field measurements made at a single wavelength can be evaluated, that is, be transformed into a meaningful signal, in a much more simple manner.

More specifically, the present invention is based upon the concept that measurements for determination of ethanol concentration in an aqueous medium should be made at a selected or "unique" wavelength where the absorbent power (or absorbency) of ethanol is significantly lower than the absorbent power (or absorbency) of water which could then be termed "relatively opaque" to light at the selected wavelength. At such a selected unique wavelength, the absorbency of pure water must be significantly higher indicating "relative opaqueness" with regard to the "relatively transparent" ethanol. In other words, the invention suggests measurement absorbency with relation to the aqueous or "background" portion of a sample rather than with relation to the absorbency of the analyte ethanol.

As used herein, "absorbency" (used synonymously with "absorption coefficient") is assumed to constitute the inverse of "transmission value" or "transmittance" and, in a quantitative sense, water would be presumed to be "relatively opaque" if it's absorbency at a given frequency in the near infrared region is at least about 3 times higher than that of the "relatively transparent" ethanol. Preferably, the unique frequency used in the method according to the invention is selected such that the absorbency of water at that frequency will be at least about 5 times higher than that of ethanol.

Further, it has been found according to the invention that, in the ethanol concentration range of main commercial interest for the beverage industry, i.e. below about 50%, by volume, and notably in the range of up to about 20%, by volume, and especially below about 10% by volume, the change of absorbency is essentially proportional to the change of the ethanol concentration. For example, passing from pure water to a mixture of water and about 4%, by volume, of ethanol would increase the transmittance by about 5%.

According to a first general embodiment the invention provides for a method of spectroscopically determining a concentration of ethanol in a test sample of an alcoholic beverage that contains a major amount of water, comprising the steps of (I) providing calibration data which establishes a relation between (a) a plurality of transmission values of an electromagnetic radiation in the near infrared region, measured at a unique wavelength at which water is relatively opaque to the radiation while ethanol is relatively transparent to the radiation, of a plurality of calibration samples of the beverage containing ethanol in differing known concentrations, and (b) the known concentrations of ethanol in the said plurality of calibration samples;

(II) measuring at least one light transmission value of the test sample at the said unique wavelength at which the calibration curve was established; and (III) transforming the at least one light transmission value of the test sample, by means of the relation which is established by the said calibration data, into an indication of the concentration of ethanol in the test sample.

According to a second general embodiment, the invention provides an apparatus for spectroscopically determining a concentration of ethanol in a test sample of an alcoholic beverage that contains a major amount of water, comprising:

(I) first means for providing calibration data which establishes a relation between (a) a plurality of transmission values of an electromagnetic radiation in the near infrared region, measured at a unique wavelength at which water is relatively opaque to the radiation while ethanol is relatively transparent to the radiation, of a plurality of calibration samples of the beverage containing ethanol in differing known concentrations, and (b) the known concentrations of ethanol in the said plurality of calibration samples;

(II) second means for measuring at least one light transmission value of the test sample at the said unique wavelength at which the calibration curve was established; and (III) third means for transforming the at least one light transmission value of the test sample, by means of the relation which is established by the said calibration data, into an indication of the concentration of ethanol in the test sample.

PREFERRED EMBODIMENTS OF THE INVENTION

The method according to the invention can be carried out with conventional means for measuring the light transmission value of the test sample at the selected unique wavelength at which the calibration data were established. Further, conventional algorithm processors can be used to transform the light transmission value of the test sample on the basis of the calibration data into an indication of the concentration of ethanol in the test sample.

It has been found according to the invention that the following wavelengths are suited for the invention: 0.98 µm±0.1 µm, 1.3 µm±0.13 µm (preferred), and 1.45 µm±0.15 µm.

For reasons of proportionality as indicated above, the method according to the invention is preferably used to determine ethanol concentrations of aqueous beverages containing not more than about 50%, by volume, and preferably not more than about 20%, by volume, of ethanol, such as beer and wine.

Further, as will be apparent to those experienced in the art, effects of other beverage constituents, such as sugar, carbon dioxide, and/or flavour constituents upon the results of ethanol determination are compensated because of the composition of the calibration samples which contain such other constituents in the same manner as the sample.

According to an embodiment preferred for many uses, the method according to the invention is carried out using an emitter, e.g. a light emitting diode (LED), for the electromagnetic radiation at a wavelength selected from one of: 0.98 µm±0.1 µm, 1.3 µm±0.13 µm, and 1.45 µm±1.5 µm; and a conventional sensor for radiation having the selected wavelength, e.g. a photo detector. The sample can be held in a cell between the emitter and the sensor provided, of course, that window portions, at least, of the cell for passage of the radiation through the sample are essentially transparent to the radiation at the selected wavelength.

When using an LED as the emitter or light source, the light beam emanating from the emitter will normally be polarized to some degree, and this should be taken into consideration when selecting the other optical components of the apparatus according to the invention. For example, the optically transparent portions or "windows" of the cell means should be below the so called Brewster angle, for example, with a window made of artificial sapphire at an angle of 60.4°, and the optical components should be aligned to avoid "bi-refringence" effects of polarization rotation.

BRIEF EXPLANATION OF THE DRAWINGS

The invention will be further explained by means of the drawing in which.

DETAILED EXPLANATION OF THE DRAWINGS

Figure 1:
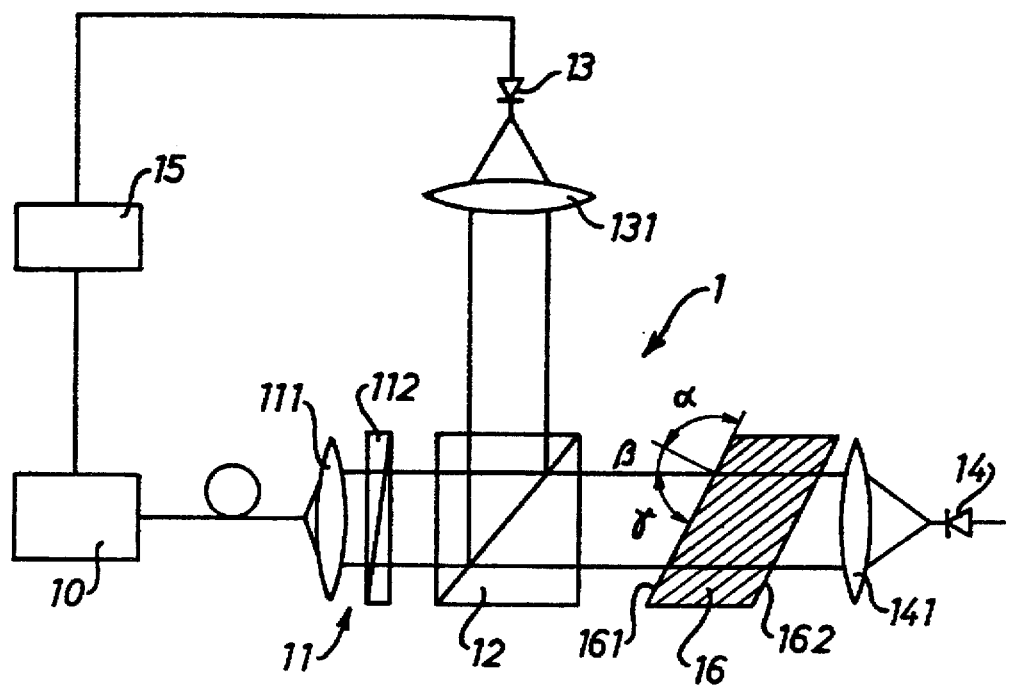
FIG. 1 is a diagrammatic representation of means used which are suitable for carrying out the inventive method.

Specifically, FIG.1 illustrates, in a diagrammatic manner, a system 1 for carrying out the method according to the invention. Light source 10 is an emitter for infrared radiation having a wavelength in the near infrared at one of the unique values specified above, preferably of about 1.3 µm±0.13 µm, and may be a commercial light emitting diode (LED), a laser or other source of substantially monochromatic radiation. Preferably, the light emanating from source 10 is transmitted via an optical fibre to an optical system 11 comprising a lens 111 and a polarizer 112. The polarized light emanating from polarizer 112 impinges upon a conventional beam splitter 12 so as to reflect a first portion of the light via lens 131 to a photodetector 13 that is sensitive to the light emitted from light source 10. The electric signal produced by photodetector 13 is fed into an electronic monitor 15 of the type known to those experienced in the art for monitoring the output of light source 10.

The non-reflected second portion of the light from source 10 is passed through a sample holder or cell 16 having a window or entry surface 161 inclined by an angle β known in the art as the "Brewster angle". In an apparatus according to the invention as illustrated in FIG. 1, the entry window 161 as well as the outlet window 162 would be of a suitably transparent (for the selected wavelength in the near infrared region) material, e.g. artificial sapphire (molten $Al_2O_3$) in which case the Brewster angle for the transition from air to sapphire would be 60.4°.

A portion of the light passing through cell 16 will be absorbed by the liquid sample but, since the absorption of all sample constituents except the ethanol portion will be compensated by calibration, it is actually the reduction of absorption caused by the ethanol constituent of the sample that is the measuring parameter of interest (hence "inverse" spectroscopy according to the invention).

The light emanating from cell 16 through window 162 passes lens 141 and impinges upon photodetector 14 of the same type as detector 13. The electric signal produced by detector 14 is passed, in a manner not illustrated in FIG.1, to an evaluation unit, e.g. a conventional algorithm processor, where the calibration data are stored electronically and where the signal produced by detector 14 is converted into an indication of the ethanol content of the sample in cell 16.

Figure 2:
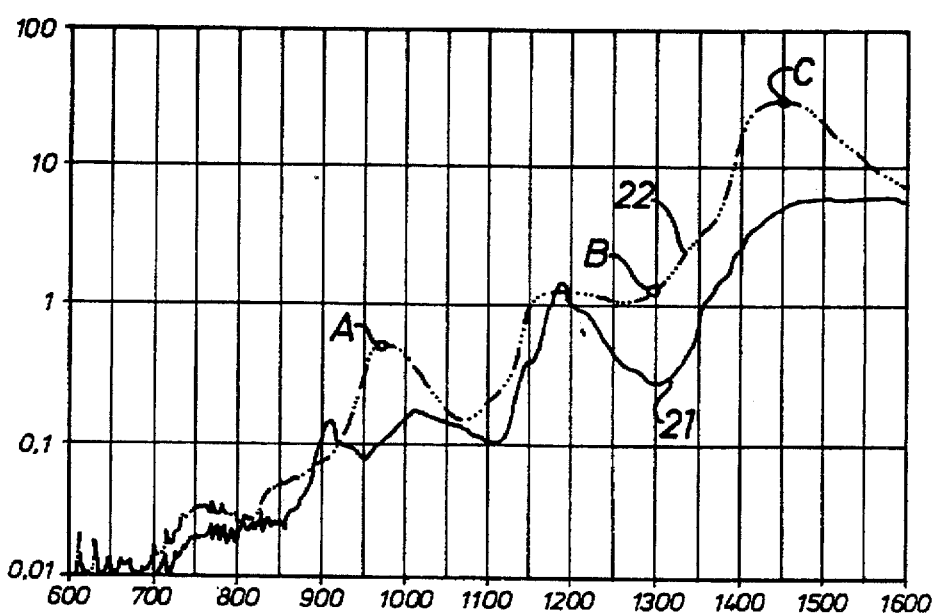
FIG. 2 is a diagram showing the relations between the absorbency of light, expressed in terms of the absorption coefficient, and the frequency used for pure water and pure ethanol, respectively.

FIG. 2 shows the absorption curves 21 (for pure ethanol) and 22 (for pure water); The ordinate shows the absorption coefficient in units of $(cm^{-1})$ while the abscissa indicates the wavelength. As will be apparent from FIG. 2, the absorption coefficients of ethanol and water differ at unique wavelengths as marked at A, B and C to the extent that ethanol is "relatively transparent" while water is "relatively opaque" in the sense that the absorption coefficient of water is at least twice as high as that of ethanol. Preferably, the absorption coefficient of the "opaque" portion (water plus any other constituents of the sample except ethanol) of the sample is at least about 5 times higher than that of the "transparent" sample portion, i.e. ethanol.

Figure 3:
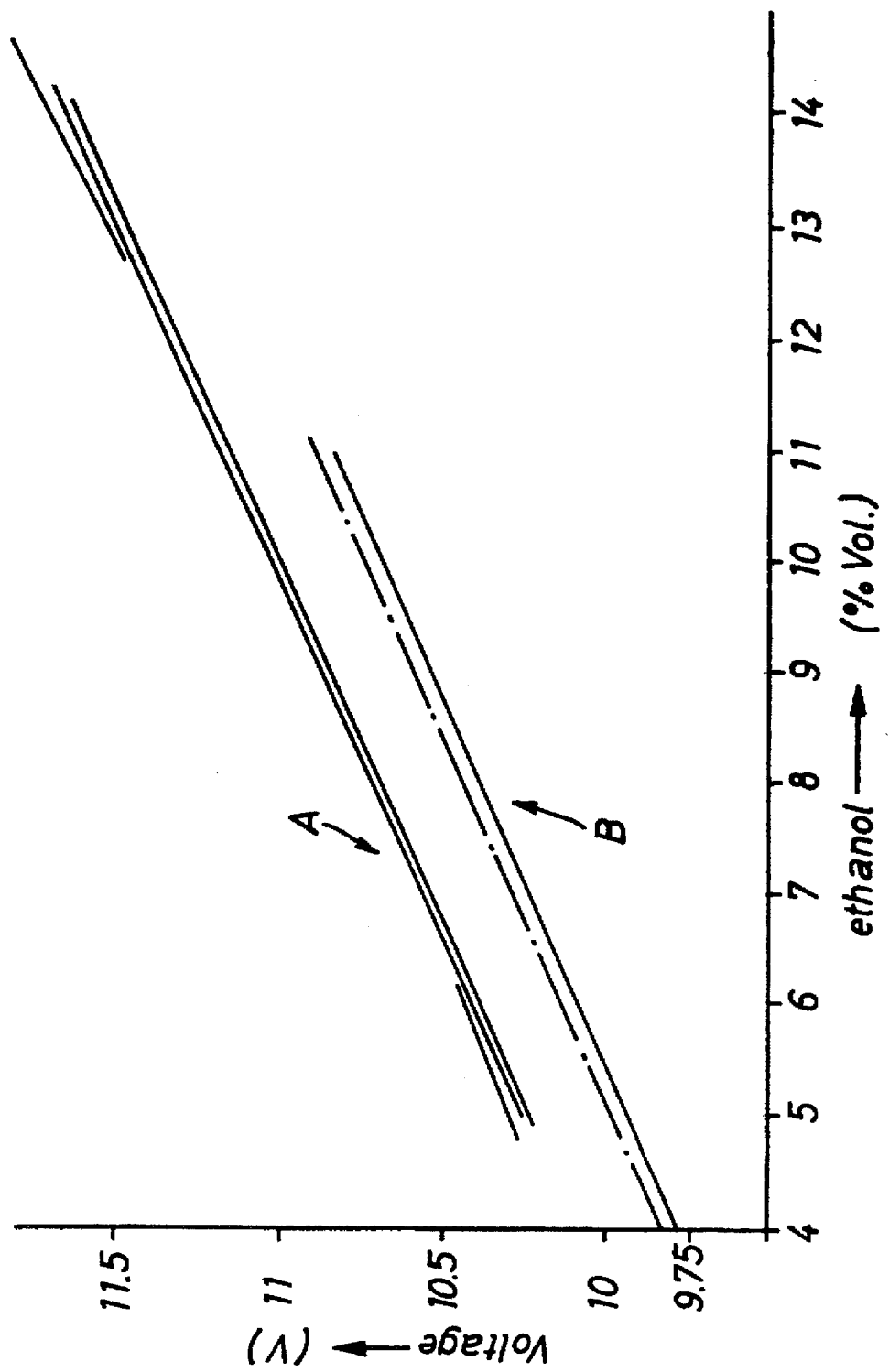
FIG. 3 is a diagram of the type suitable for calibration of the method according to the invention when measuring alcohol concentrations of various beers.

FIG. 3 is a diagram obtained from a variety of beer samples. The ordinate indicates the voltage V measured by the photodetector while the abscissa indicates the alcohol content of the calibration liquids. Lines of group A were obtained from a number of different commercial beers to which pure ethanol had been added for calibration purposes. Lines of group B were obtained from mixtures of pure ethanol and pure water with and without dissolved carbon dioxide.

In the course of studies leading to the present invention, it was found—as shown in FIG. 3—that the lines passing through the uncorrected transmission intensities versus ethanol concentrations for (A) a particular alcoholic beverage, such as beer, with additions of pure ethanol, or (B) for aqueous solutions of pure ethanol, have substantially the same slope (0.156±0.002 Volt per volume-percent (% Vol) ethanol, when measured at an ambient temperature (e.g. 22° C.).

The lines of group A measured for four different commercially available brands of beer (Cardinal Lager 4.8% Vol, Carlsberg 5.0% Vol, Heineken 5.0% Vol, Tuborg 5.3% Vol) lie very close together: their intercepts with the ordinate are quite similar. Furthermore, lines A show that the uncorrected ("raw") light transmission intensities depend upon two sets of factors: (i) factors characteristic of the beer (e.g. ethanol content, temperature, sugar content, carbon dioxide content, and colouring matter content) and (ii) factors characteristic of the apparatus (e.g. intensity of the light source, sensitivity of the photodetector, alignment and configuration of the optical elements).

According to a preferred embodiment of the invention and with reference to FIG. 1: in order to compensate for the apparatus-dependent factors (ii) the light intensity transmitted through cell 16 is divided by the light intensity reflected from beam splitter 12. Preferably, photodetectors 13 and 14 and associated circuitry (not shown in FIG. 1) for converting a detected light intensity into electric signals should be matched so as to ascertain that they track each other when the temperature varies. Any further apparatus-dependent factors can be diagnosed by zero calibration in pure water because the absorbency of pure water at the selected wavelength should bear a constant relationship to the measured intercept for beer.

In other words, there should be a spacing between the calibration lines for pure water and for any particular beer which depend only on the character (composition and state) of the beer. Accordingly, such measurements will effectively eliminate or compensate the set of factors (ii) and yield a result which depends only on (i) the character of the beer.

Preferably, this result will then be compensated for the temperature. The calibration lines, such as lines (A) in FIG. 3, will present the dependence of the compensated light transmission intensity upon ethanol concentration at a standard temperature. If the other beer-dependent factors (sugar, carbon dioxide, color constituents) remain constant, a measured compensated light transmission intensity can be converted into the ethanol content value by reference to this line.

If the other factors are not essentially constant, additional compensation steps may become necessary; however, monitoring ethanol content in the process of an essentially continuous beer production of a particular brand will not normally require such additional compensation. When required for particular reasons, additional compensation may become necessary but this is feasible with conventional methods known in the art.

Straightness of lines A in FIG. 3, (i.e. operation at ethanol concentrations where linearity is maintained) is not believed to be a critical issue for the present invention, notably since many commercially important areas of beverage production operate with relatively low ethanol concentrations of typically below about 20% Vol and preferably below about 10% Vol; however, with increasing ethanol content, linearity of the calibration curves need not be obtained for practising the method according to the invention because, in practice, the slope or shape of the calibration function, or line, can be taken as a constant and it is sufficient for practical applications of the invention to measure only one transmission for a single calibration sample having a known ethanol concentration for tracing the whole calibration line or curve.

The ethanol concentration of a calibration sample, e.g. beer, can be determined by standard methods well-known in the analytical art, e.g. by distillation as described in Institute of Brewing Recommended Methods of analysis, 1991, p. 220, Method 8.5.3, or by means of another calibrated instrument, such as the analyzer sold by the Scaba Company.

Mathematically speaking, the calibration data or curve when operating in the essentially linear region can be represented by the equation:

Light transmission=Intercept+Slope·Ethanol concentration

When slope, concentration and transmission are known for the calibration sample, the intercept can be calculated. During actual measurement of a sample having an unknown ethanol content, only a light intensity is measured, and a conventional microprocessor can be used to transform this value into the ethanol concentration of the sample.

If the calibration curve is significantly curved, a similar but slightly more complicated procedure can be used. In this case, other terms, e.g. a quadratic term, would appear in the calibration equation and two or more pairs of transmission/concentration data will be used to determine the associated constants. Algorithms for numerical treatment of calibration data of this type by computer are commonly available. Still, for actual measurement, a single light intensity measurement will be sufficient to calculate the ethanol concentration as is the case with substantially linear calibration curves.

EXAMPLES

In the manner described above using a system substantially as illustrated in FIG. 1, the relationship between the uncompensated or "raw" light transmissions (at 22° C.) of four solutions of ethanol in distilled water having ethanol concentrations of 4, 6, 8, and 10% Vol, respectively, and their ethanol content was determined. This relation was found to be:

Transmitted light intensity [V]=9.136 [V]+0.1562 [V/% Vol]·ethanol concentration [% Vol]

Then, the light transmissions were measured for the same series of aqueous solution of ethanol at the same temperature but saturated with carbon dioxide at 2 bar partial pressure. The slope of the calibration curve shifted by an insignificant amount to 0.1572 [V/% Vol] but the intercept increased to 9.191 [V].

Now, it was verified that the slopes of similar lines derived from measurement on commercial beer brands were all very close to that of the aqueous ethanol solutions:

Tuborg 0.1583 [V/% Vol],

Cardinal 0.1586 [V/% Vol]

Carlsberg 0.1545 [V/% Vol]

Heineken 0.1549 [V/% Vol].

A sample of Tuborg brand beer containing 5.3% Vol of alcohol produced a light transmission signal of 10.370 [V]. Hence, the equation for conversion of light transmission values to ethanol concentrations for this brand was calculated to be:

Light intensity [V]=10.370 [V]+0.1562 [V/% Vol]·{ethanol concentration [% Vol]−5.3 [% Vol]}

The precision of the voltage measurement was better then ±1 mV. Accordingly, the resolution of the ethanol concentration measurement using this formula is 0.0065% Vol.

The above illustrations and the example have been given for the purpose of illustration, not limitation.

We claim:

1. A method of spectroscopically determining a concentration of ethanol in a test sample of an alcoholic beverage that contains a major amount of water, comprising the steps of:
   (I) providing calibration data which establish a relation between
      (a) a plurality of transmission values of electromagnetic radiation in the near infrared region, measured at a unique wavelength at which said water is relatively opaque to said radiation while said ethanol is relatively transparent to said radiation, of a plurality of calibration samples of said beverage containing said ethanol in differing known concentrations, and
      (b) said known concentrations of ethanol in said plurality of said calibration samples;
   (II) measuring at least one light transmission value of said test sample at said unique wavelength at which said calibration data were established; and
   (III) transforming said at least one light transmission value of said test sample, by means of said relation established by said calibration data, into an indication of said concentration of said ethanol in said test sample;
   wherein said unique wavelength is selected from the group of wavelengths consisting of about 0.98 μm, about 1.3 μm, and about 1.45 μm.

2. The method of claim 1, wherein said alcoholic beverage contains less than 10% by volume of said ethanol.

3. The method of claim 1, wherein said alcoholic beverage is beer.

4. An apparatus for spectroscopic determination of a concentration of ethanol in a test sample of an alcoholic beverage that contains a major amount of water, comprising:
   (I) first means for providing calibration data which establish a relation between
      (a) a plurality of transmission values of electromagnetic radiation in the near infrared region, measured at a unique wavelength at which said water is relatively opaque to said radiation while said ethanol is relatively transparent to said radiation, of a plurality of calibration samples of said beverage containing said ethanol in differing known concentrations, and
      (b) said known concentrations of ethanol in said plurality of said calibration samples;
   (II) second means for measuring at least one light transmission value of said test sample at said unique wavelength at which said calibration data were established; and
   (III) third means for transforming said at least one light transmission value of said test sample, by means of said relation established by said calibration data, into an indication of said concentration of said ethanol in said test sample;
   wherein said unique wavelength is selected from the group of wavelengths consisting of about 0.98 μm, about 1.3 μm, and about 1.45 μm.

* * * * *